(12) United States Patent
Wright et al.

(10) Patent No.: US 9,597,532 B2
(45) Date of Patent: Mar. 21, 2017

(54) BREATHING APPARATUS, AND METHOD FOR CONTROLLING TEMPERATURE FLUCTUATIONS

(71) Applicant: TDA Research, Inc., Wheat Ridge, CO (US)

(72) Inventors: John David Wright, Morrison, CO (US); Robert James Copeland, River Ridge, CO (US); Girish Srinivas, Broomfield, CO (US); Steven Charles Gebhard, Golden, CO (US); Michael Edward Karpuk, Boulder, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 801 days.

(21) Appl. No.: 13/912,858

(22) Filed: Jun. 7, 2013

(65) Prior Publication Data

US 2014/0360500 A1   Dec. 11, 2014

(51) Int. Cl.
*A62B 18/08* (2006.01)
*A62B 9/00* (2006.01)
*A62B 23/02* (2006.01)

(52) U.S. Cl.
CPC ............... *A62B 9/003* (2013.01); *A62B 18/08* (2013.01); *A61M 2205/3606* (2013.01); *A62B 23/02* (2013.01)

(58) Field of Classification Search
CPC ...... A61M 2205/36; A61M 2205/3606; A61M 2205/362; A61M 2205/3633; A61M 2205/3646; A62B 9/003; A62B 23/003; F28D 2020/0004; F28D 2020/0017; F28D 20/056; F28D 20/006; F28D 20/003
See application file for complete search history.

(56) References Cited

U.S. PATENT DOCUMENTS

| | | | | |
|---|---|---|---|---|
| 2,610,038 A | * | 9/1952 | Phillips | A62B 23/02 128/201.13 |
| 3,099,987 A | * | 8/1963 | Bartlett, Jr. | A62B 9/003 128/201.13 |
| 4,136,691 A | | 1/1979 | Ebeling et al. | |
| 4,301,792 A | * | 11/1981 | Pasternack | A62B 9/003 128/202.26 |
| 4,314,566 A | * | 2/1982 | Kiwak | A61M 16/1075 128/202.26 |

(Continued)

*Primary Examiner* — Justine Yu
*Assistant Examiner* — Douglas Sul
(74) *Attorney, Agent, or Firm* — Renner, Otto, Boisselle & Sklar, LLP (57) ABSTRACT

A wearable breathing apparatus includes a thermal capacitor that a user inhales and exhales through. Inhaled air is cooled as it passes through the thermal capacitor, and exhaled air cools the material of the thermal capacitor for the next breathing cycle. The breathing apparatus may be used by a firefighter, for example, as a lightweight apparatus to enable the firefighter to safely breathe dangerously heated air, for example while in a fire shelter, that may otherwise cause injury to the user. The breathing apparatus advantageously does not require external power for cooling. The thermal capacitor may also be used as a part of a rebreather that uses a scrubber that removes carbon dioxide from exhaled air, for rebreathing. Further, the thermal capacitor may be used for other purposes, such as in recirculation of building air.

14 Claims, 4 Drawing Sheets

(56) References Cited

U.S. PATENT DOCUMENTS

| | | | | |
|---|---|---|---|---|
| 4,829,997 A | * | 5/1989 | Douwens | A61M 16/1075 |
| | | | | 128/201.13 |
| 5,193,347 A | * | 3/1993 | Apisdorf | A42B 3/285 |
| | | | | 2/171.3 |
| 5,202,150 A | * | 4/1993 | Benson | B27K 3/0242 |
| | | | | 427/376.2 |
| 5,269,293 A | * | 12/1993 | Loser | F25B 17/08 |
| | | | | 128/204.15 |
| 5,435,299 A | | 7/1995 | Langman | |
| 5,524,616 A | | 6/1996 | Smith et al. | |
| 5,570,684 A | * | 11/1996 | Behr | A61M 16/06 |
| | | | | 128/201.13 |
| 5,628,308 A | | 5/1997 | Harges, Jr. et al. | |
| 5,662,161 A | * | 9/1997 | Hughes | A62B 9/003 |
| | | | | 128/201.13 |
| 5,823,188 A | | 10/1998 | Harges, Jr. et al. | |
| 5,896,856 A | * | 4/1999 | Frasier | A62B 9/003 |
| | | | | 128/204.15 |
| 5,964,218 A | | 10/1999 | Smith et al. | |
| 6,615,906 B1 | * | 9/2003 | Fieback | A01K 5/0114 |
| | | | | 165/10 |
| 7,721,732 B2 | | 5/2010 | Bagby | |
| 2010/0024826 A1 | | 2/2010 | Sullivan, Jr. | |

* cited by examiner

| Material | Form | Size (mm) | k (W/m K) | Cp (kJ/kg K) | ρ (kg/m³) | Void fraction |
|---|---|---|---|---|---|---|
| Glass | Spheres | 1.00 | 0.97 | 0.67 | 2599 | 38% |
| Stainless steel | Spheres | 1.00 | 13.85 | 0.42 | 8110 | 38% |
| Stainless steel | Screen | 0.15 | 13.85 | 0.42 | 8110 | 38% |
| Cordierite | Honeycomb | 1.00 | 2.99 | 1.47 | 1769 | 72% |
| Aluminum | Spheres | 2.00 | 173 | 0.90 | 2698 | 38% |
| Polypropylene | Mesh | 0.15 | 0.12 | 0.46 | 855 | 72% |
| Polyethylene | Muffler | 0.10 | 0.32 | 2.25 | 855 | 38% |

BREATHING APPARATUS, AND METHOD FOR CONTROLLING TEMPERATURE FLUCTUATIONS

BACKGROUND OF THE INVENTION

Technical Field of the Invention

The invention is in the field of controlling temperature fluctuations in periodic gas flows. One specific application is in the field of breathing apparatus, such as are used by firefighters or miners.

Description of the Related Art

One situation where cooling of periodic air flow is required is for wildland firefighters in fire shelters. When trapped by a wildfire, firefighters can use a portable metallized shelter that provides some protection from the extreme temperatures and toxic gases generated in the event of a burnover. Entrapment conditions caused by a wildfire, however, are often harsh enough to lift the shelter's edges or tear the shelter, letting smoke and superheated air inside. Should the fire shelter become compromised, the shelter does little to protect the firefighter from smoke, toxic gases (e.g., carbon monoxide (CO)), or superheated air, and the respiratory tract can be damaged very quickly. In order to avoid respiratory damage, inhaled air may need to be at a temperature of 48° C. (119° F.) or cooler.

Another situation in which cooling of respiratory air is useful is in rebreathing apparatus, such as those used by miners. Rebreathers are used in mine rescue, firefighting, and other applications where portable breathing air is needed for periods of time greater than can be provided by a standard open-circuit air pack (a self-contained breathing apparatus (SCBA)). In mine rescue, rebreathers may be used when reentering a mine after an accident to rescue stranded miners and/or perform other tasks necessary to bring the mine back online. Standard mine rescue rebreathers supply oxygen for 4 hours.

Another type of rebreather is a 10-30 minute self-contained, self-rescuer (SCSR) that is carried by individual miners or kept in close proximity so that in case of an emergency, the SCSR can be donned and the miner can escape to a safe location. All rebreathers conserve air (and therefore minimize size and weight) by recirculating exhaled air through a system that removes carbon dioxide ($CO_2$) with an alkali scrubber (commonly soda-lime or lithium hydroxide), while metering oxygen into the return air from a small compressed gas cylinder to maintain a desired inhaled oxygen ($O_2$) concentration, for example a concentration of at least 19.5%. Considerable heat is generated when $CO_2$ is removed using alkaline scrubbers, and additional heat is generated when moisture in the exhaled breath is condensed. In full size (e.g., rescue size) commercial devices, this heat is removed using ice packs that are installed into the unit just prior to use. In the smaller SCSR, there is no room for an ice pack so the unit relies on its thermal mass to absorb the heat. Depending on the ambient conditions, when the SCSR is used, its mass may or may not be sufficient to keep the temperature of the inhaled air below the requirement of 48° C. (119° F.).

SUMMARY OF THE INVENTION

A periodic gas flow is directed through a porous material that acts as a thermal capacitor, cooling the flow in one direction, and warming the flow in the opposite direction.

A breathing apparatus includes a thermal capacitor. Air for inhalation is cooled by passing through the thermal capacitor, and relatively cool exhaled air is also passed through the thermal capacitor in the opposite direction, cooling the porous material in the thermal capacitor.

A rebreather includes a thermal capacitor through which air to be breathed by a user is passed, to cool the air to be inhaled. Relatively cool air exhaled by the user is also passed through the thermal capacitor, in the opposite direction, cooling porous material in the thermal capacitor.

According to an aspect of the invention, a wearable breathing apparatus for controlling temperature of air inhaled by a user includes: a respiratory conduit that the user of the apparatus inhales and exhales through; and a thermal capacitor operatively connected to the respiratory conduit such that inhaled air and exhaled air passing through the respiratory conduit and also passes through a porous material of the thermal capacitor. The porous material has a time constant, where a lumped thermal capacitance (the mass of the porous material multiplied by the specific heat of the porous material) is multiplied by the thermal resistance to heat transfer (the reciprocal of the heat transfer coefficient multiplied by the surface area available for heat transfer) of the porous material, that is at least 0.5 seconds. The time constant is given by $\tau = mC_p/hA$, where m is the mass and $C_p$ is the specific heat of the porous material, h is the heat transfer coefficient, and A is the area for heat transfer.

According to another aspect of the invention, a method of cooling breathing air inhaled by a person includes the steps of: passing the air to be inhaled through a porous material of a thermal capacitor, with the porous material cooling the air to be inhaled; and exhaling air through the porous material, thereby cooling the porous material. The porous material has a time constant, where a lumped thermal capacitance (the mass of the porous material multiplied by the specific heat of the porous material) is multiplied by the thermal resistance to heat transfer (the reciprocal of the heat transfer coefficient multiplied by the surface area available for heat transfer) of the porous material, that is at least 0.5 seconds.

According to yet another aspect of the invention, a method of reducing temperature fluctuations in a periodic gas flow includes the step of directing the periodic flow through a porous material of a thermal capacitor. The thermal capacitor cools gas flowing in a first direction, and warms gas flowing in a second direction that is opposite the first direction. The porous material has a time constant, where a lumped thermal capacitance (the mass of the porous material multiplied by the specific heat of the porous material) is multiplied by the thermal resistance to heat transfer (the reciprocal of the heat transfer coefficient multiplied by the surface area available for heat transfer) of the porous material, that is at least one period of the periodic gas flow.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The annexed drawings, which are not necessarily to scale, show various features of the invention.

DETAILED DESCRIPTION

A wearable breathing apparatus includes a thermal capacitor that a user inhales and exhales through. Inhaled air is cooled as it passes through the thermal capacitor, and exhaled air cools the material of the thermal capacitor. The breathing apparatus may be used by a firefighter, for example, as a lightweight apparatus to enable the firefighter to safely breathe otherwise dangerously heated air, for example while in a fire shelter, that may otherwise cause injury to the user. The breathing apparatus advantageously does not require external power for cooling. The thermal capacitor may also be used as part of a rebreather that uses a scrubber that removes carbon dioxide from exhaled air, for rebreathing. Further, the thermal capacitor may be used for other purposes, such as in the recirculation of building air.

Figure 1:
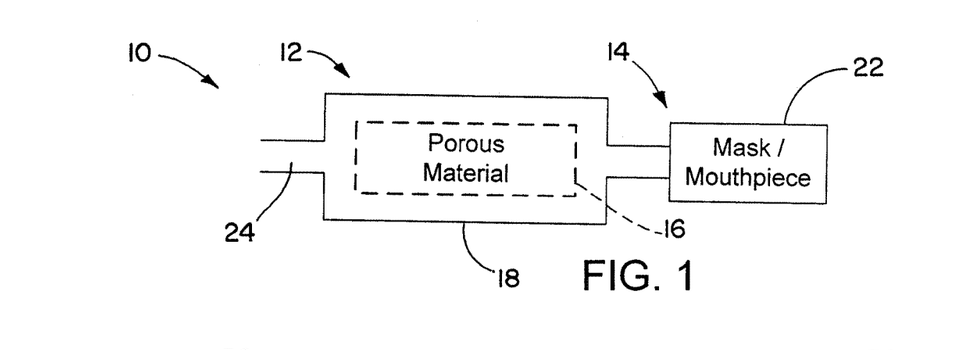
FIG. 1 is a schematic diagram of a breathing apparatus, according to an embodiment of the invention.

FIG. 1 is a schematic diagram of a wearable breathing apparatus 10 that includes a thermal capacitor 12 and a respiratory conduit 14. The thermal capacitor 12 includes a porous material 16, and a casing 18 that surrounds and contains the porous material 16. The respiratory conduit 14 is attached to one end of the casing 18, and may include a mask or mouthpiece 22 for the user to breathe through. The casing 18 also includes an external opening 24, which may be on an opposite side of the casing 18 from wherein the conduit 14 joins the casing 18. Alternatively, the opening 24 omitted or augmented by using a casing 18 that contains holes, slots or other penetrations to permit a radial flow design.

The mask or mouthpiece 22 may be a mask that fits over all or part of a user's face, for example fitting over at least the mouth and nose of the user. Or the mouthpiece/mask 22 may be a mouthpiece that the user inserts at least part of into his or her mouth, perhaps used in combination with a nose clip to prevent breathing through the user's nose. The mask or mouthpiece 22 may be made of suitable materials, for example including suitable plastics.

Any of a wide variety of materials may be used for the porous material 16. The porous material 16 may be a woven and/or mesh material, for example made from a suitable polymer material such as polypropylene, polyester or polyethylene. Smaller mesh sizes (and/or looser weave) result in an acceptable pressure drop, increased cooling effect, and decreased size of the thermal capacitor. However, in principle a wide variety of mesh sizes and/or weaves can be used. A suitable mesh porous material is a spiral wrap polypropylene mesh, which may be used in a radial flow device. Alternatively, the porous material 16 may be a ceramic porous material, for example a cordierite porous material. An example is a 400 cells-per-square-inch (CPSI) honeycomb cordierite monolith material. Other possible configurations for the porous material 16 include a bed of spheres, particles, or pellets of material that is able to absorb heat. Examples of materials for such configurations include aluminum, other metals, glass, or ceramic spheres, having diameters of 1 mm or 5 mm. A variety of other materials/configurations may be employed instead of or in addition to those described above. A suitable screen (not shown in FIG. 1) may be used to retain the porous material 16 in the container 18.

Depending on the type of porous material 16 used, the void fraction of the thermal capacitor 12 may vary greatly. Mesh and/or woven porous materials may result in a relatively high void fraction, for example a void fraction of 0.72. Spheres may result in a relatively low void fraction, for example a void fraction of 0.38. It may be advantageous to have the void fraction be at least 0.3, or at least 0.5, to minimize pressure drop and breathing resistance.

The material for the casing 18 may be any of a wide variety of suitable rigid materials. Examples include metals, for example steel, or a variety of suitable plastics or other polymers.

Figure 2A:
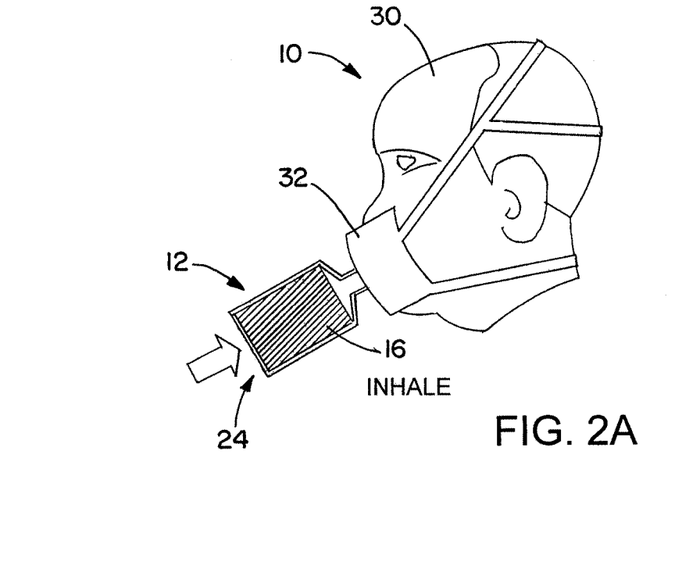
FIG. 2A is an illustration of air flow through the device of FIG. 1, during inhalation.
Figure 2B:
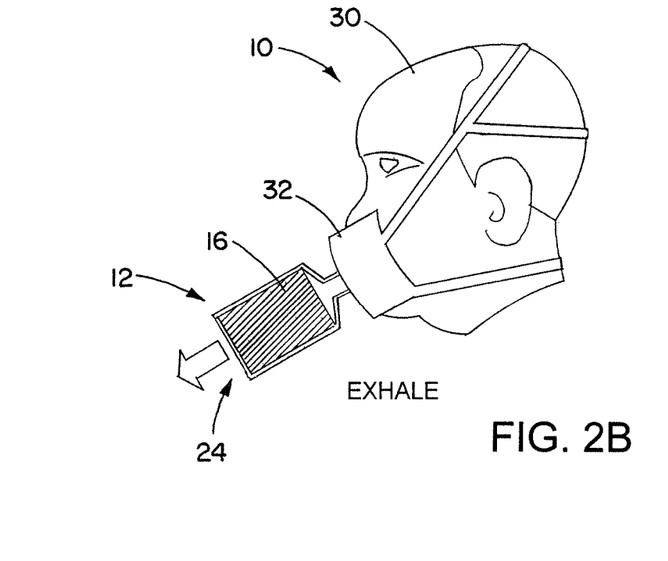
FIG. 2B is an illustration of air flow through the device of FIG. 1, during exhalation.

The wearable breathing apparatus 10 works by having the user breathe (inhale and exhale) through the thermal capacitor 12. This process is illustrated in FIGS. 2A and 2B, in which the breathing apparatus is held onto a user 30 with a mask 32. FIGS. 2 and 3 show flow through an axial flow device. In a radial flow device, inhaled and exhaled air would flow through the sides of the thermal capacitor 12. During inhalation (FIG. 2A), the user 30 draws external air into the thermal capacitor 12 through the opening 24. The air passes through the porous material 16 and the respiratory conduit 14, from where it is received by the user 30 through the mask 32. The air is cooled as it passes through the thermal capacitor 12, with heat being transferred from the incoming air to the porous material 16.

Exhalation (FIG. 2B) proceeds by the same path, albeit in the opposite direction, with the user exhaling air through into the mask 32 and the respiratory conduit 14 into the thermal capacitor 12. The exhaled air passes through porous material 16, with heat being transferred from the porous material 16 to the exhaled air, cooling the porous material 16. Finally the exhaled air exits the apparatus through the opening 24. The back-and-forth flow of air through the thermal capacitor 12 both cools the inhaled air to a safe temperature, and provides sufficient cooling to the porous material 16 (by exhaling moist, relatively cool air through it) so that the porous material 16 can continue to cool inhaled air.

The thermal capacitor 12 is configured to provide the desired repeated cooling of inhaled air. The porous material 16 may have a time constant, which is the lumped thermal capacitance of the porous material 16 multiplied by the thermal resistance of the porous material 16, that is at least 0.5 seconds. Alternatively, the time constant of the porous material 16 may have other values, for example being at least 1 second, or at least 3 seconds. The lumped thermal capacitance is a parameter related to how much heat energy the porous material can absorb. It is an approximation, with the porous material assumed to uniformly change temperature (no temperature gradients in the material) and with the driving force for temperature change being only convective heat transfer at the solid surface. The time constant $\tau$ can be represented as $\tau = mC_p/hA$, where m is the mass of the porous material 16, $C_p$ is the specific heat of the porous material 16, h is the heat transfer coefficient between the air and the surface of the porous material 16 and A is heat transfer area between the air and the porous material 16. The heat transfer coefficient is essentially constant for laminar flow through small channels and is not greatly affected by the air flow. The area for heat transfer depends on the porosity and internal geometry of the porous material.

In passing through the thermal capacitor 12 the inhaled air exponentially decreases in temperature from the temperature of the air surrounding the apparatus 10, toward a temperature of the porous material 16. As a rough measure, the time constant $\tau_{device}$ may be compared with the breath rate of a typical user, which may be taken as about 1.8 breaths per second.

The thermal time constant $\tau$ that is used is determined by the amplitude ratio (AR) for the response of a first order system to a sinusoidal input (forcing function). The amplitude ratio is determined from the temperatures of the hot and cool air streams: $AR=T_{cool}/T_{hot}$ with the temperatures in absolute units (Kelvin or Rankine). The amplitude ratio for a first order system with a sinusoidal forcing function is given by $AR=(\tau^2\omega^2+1)^{-1/2}$, where $\tau$ is the time constant and $\omega$ is the breathing frequency in angular units (i.e., $\omega=2\pi f$, where f is the frequency in $sec^{-1}$), as is described in Coughanowr and Koppel "Process Systems Analysis and Control," McGraw Hill, 1965. For any given value of the periodic flow frequency ($\omega=2\pi f$) such as the breathing rate, and a value of AR (determined by the hot and cool air temperatures), the time constant $\tau$ can be calculated. Since the time constant $\tau=mC_p/hA$, the combinations of mass, Cp, h, and A that give the required $\tau$ are all reasonable configurations, at least from a thermal analysis standpoint.

Other considerations may also go into configuring the thermal capacitor 12. For example it may be desirable for heat conduction along the direction of air flow through the porous material 16 to be minimized. Heat conduction can be numerically or analytically modeled. Numerical modeling may be accomplished using a suitable computer program such as (for example) SINDA FLUINT. The thermal capacitor may be configured from the results of numerical simulations of its operation. Using a computer model has the advantage of being able to predict the non-steady-state performance of the apparatus 10 over the course of many breathing cycles.

Another method is an analytical approach for unsteady state heat conduction in solids, such as that given in Carlslaw and Jaeger's "Conduction of Heat in Solids," Oxford, 1959. This analytical approach can be used to estimate the effect of heat conduction in the direction of flow. For example, an axial flow cordierite monolith may be analyzed by modeling the porous material as an infinite slab subjected to a sudden increase in temperature at one end (the hot air inlet). In one example configuration, a "thermal penetration depth" ($\delta$) of approximate 6.4 mm (0.25 inches) was calculated using an initial temperature of 300° F. and a breathing time of 5 seconds (very slow breathing to maximize the amount of conduction for the calculation). This means that the porous material that is more than 6.4 mm downstream of the hot end will contribute to less than 1% of any heat conduction in the flow direction, and that the thermal capacitor material downstream of this 6.4 mm section will be cooling the incoming air by the convective transfer of heat from the air to the porous material. The thermal penetration depth ($\delta$) is given by $\delta=2(\alpha t)^{1/2}$, where $\alpha$ is the thermal diffusivity and t is the breathing time. Materials that have low values of thermal diffusivity ($\alpha=k/\rho C_p$) exhibit lower heat conduction in the flow direction than materials with high thermal diffusivities (such as metals). In the equation for the thermal diffusivity ($\alpha$), k is the thermal conductivity, $\rho$ is the density, and $C_p$ is the specific heat of the material. Aluminum and other metal spheres may be used as the porous materials in the thermal capacitor because the point-to-point contact between spheres results in poor heat conduction, and thus even though aluminum and other metals are excellent conductors of heat, the effective thermal diffusivity of a packed bed of metal spheres is much lower than the thermal diffusivity of the pure metal.

The apparatus 10 may have desirable characteristics regarding size and weight. Since the apparatus 10 may be may be carried as part of an equipment pack worn by a wildland firefighter, for example, it is desirable that the size and weight be kept within limits. For example, the thermal capacitor 12 may have a mass of 0.45 kg or less (a weight of 1 pound or less). The thermal capacitor 12 may be cylindrical, and may have a length of 12.7 cm (5 inches) or less. As noted above, the air flow through the thermal capacitor 12 may be in an axial direction, in the direction of the length of the thermal capacitor 12 or in the radial direction perpendicular to the long dimension of the thermal capacitor. These values are only examples, and other values of the dimensions are possible. A typical diameter for the thermal capacitor may be about 6.7 cm (2.65 inches). The light weight and small size of the thermal capacitor 12 aids in keeping the apparatus 10 easy to carry.

The thermal capacitor 12 may have any of a large variety of other shapes, sizes, and/or configurations. Axial flow and radial flow configurations are possible alternatives. The thermal capacitor 12 may have a cross-section shape that is circular, oval, rectangular, hexagonal, otherwise polygonal, and/or an irregular shape.

Another desirable characteristic is a low pressure drop across the thermal capacitor 12 during breathing by the user. It may be desirable to limit the pressure drop across the thermal capacitor 12 to at most 500 Pa (2 inches of water column).

Figure 3A:
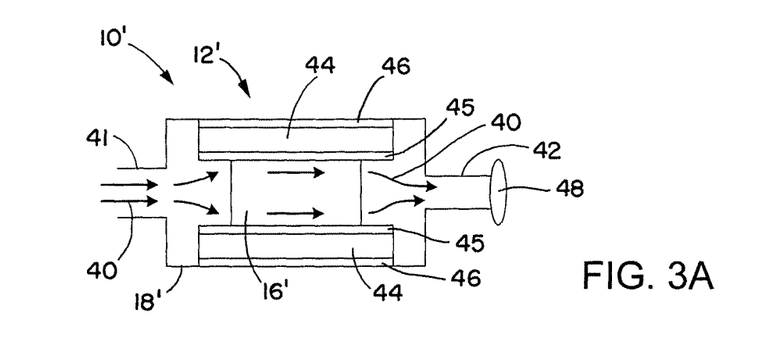
FIG. 3A is a partial cross-section view of a first specific embodiment of a breathing apparatus.
Figure 3B:
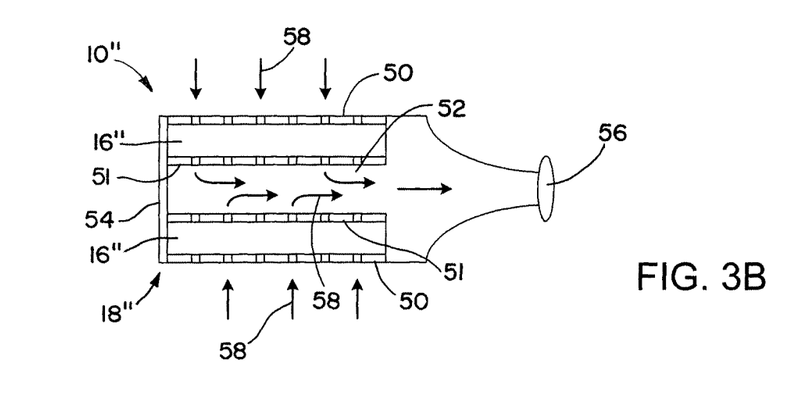
FIG. 3B is a partial cross-section view of a second specific embodiment of a breathing apparatus.

FIGS. 3A and 3B show a pair of specific embodiments of the apparatus 10 (FIG. 1), an axial (or longitudinal) flow apparatus 10' shown in FIG. 3A and a radial flow apparatus 10" shown in FIG. 3B. The apparatus 10' and 10" may be cylindrical, but may alternatively have other shapes. The axial/longitudinal flow apparatus 10' has a porous material plug 16' that is in a flow path 40 through a thermal capacitor 12' from one end 41 (an inlet for the inhalation flow shown in FIG. 3A) to an opposite end 42 of a casing 18'. The casing 18' encloses a thermal insulation layer 44, perhaps with non-permeable layers 45 and 46, such as thin layers of metal or plastic on the inner and outer surfaces of the insulation layer 44. The user uses a mouthpiece 48 for breathing into and out of.

The radial flow apparatus 10" shown in FIG. 3B has its porous material 16" contained by screens or other suitable rigid porous structures 50 and 51. The screens 50 and 51 keep the porous material 16" from passing in a radial direction, either out of the apparatus 10" or into a central channel 52. An end plate 54 of the casing 18" blocks off the end of the thermal capacitor 12" that is opposite the mouthpiece 56, and supports the screens 50 and 51 (which may be attached to the end plate 54). Flow for inhalation follows a flow path 58, through the outer screen 50, the porous material 16", and the inner screen 51, before traveling up the central channel 52 and to the mouthpiece 56.

Figure 4:
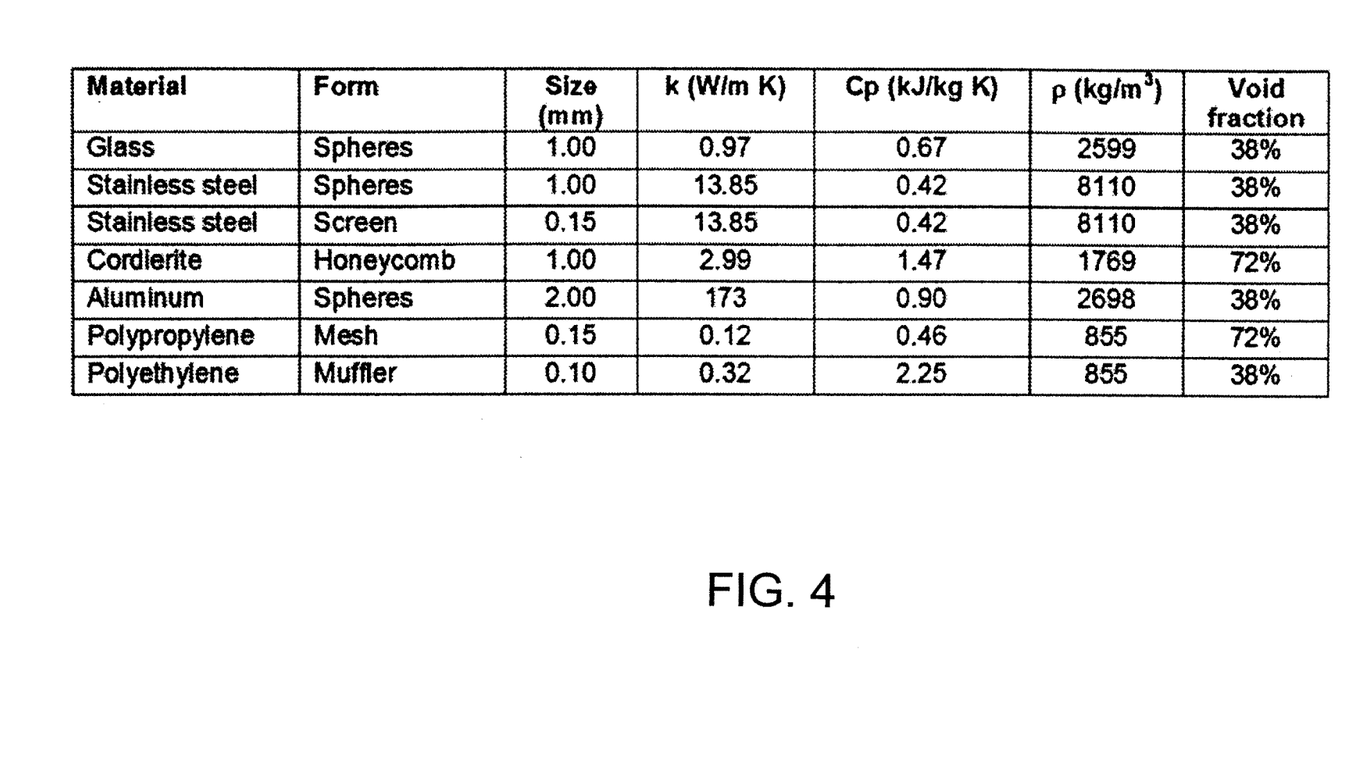
FIG. 4 is a table showing some possible materials for the thermal capacitor of the device of FIG. 1.

FIG. 4 is a table showing characteristics for a number of possible porous materials that were considered for the porous material 16.

Passing the inhaled air through the thermal capacitor 12 reduces the incoming air to a safely breathable temperature. For example, according to standards put out by the United States National Institute for Occupational Safety and Health (NIOSH), published in Section 84.103 of Title 42 of the Code of Federal Regulations, a respiratory device designed for escape purposes, and to have a service life of 15-45 minutes, will perform acceptably if the inspired air is no hotter than 48° C. (119° F.). Accordingly the thermal capacitor 12 may be configured to lower the temperature of superheated air that may be encountered in extreme firefighting conditions, such as in a fire shelter, for example air at from 120-230° C. (250-450° F.), and to continue to maintain the cooling during an operative life of the apparatus 10.

The thermal capacitor 12 may provide the additional advantage of filtering the incoming air. For example, use of a polypropylene screen (mesh and/or woven) as the porous material 16 has been found to remove particles larger than 150-300 microns (μm) from the incoming air.

Figure 5:
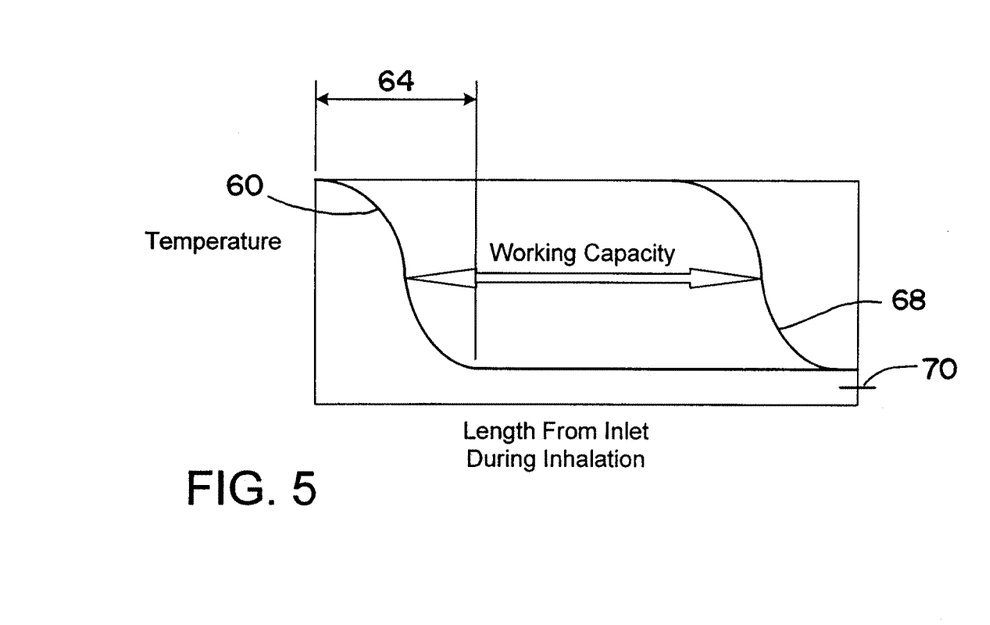
FIG. 5 is a temperature plot illustrating operation of the device of FIG. 1.

FIG. 5 shows the temperature profile within the thermal capacitor during an inhalation. The temperature profile at the start of inhalation is shown in curve 60. The air cools over a cooling length 64, which is initially near the inlet. During the inhalation the porous material 16 (FIG. 1) heats up, beginning near the inlet and moving progressively in an axial direction down the porous material 16. The limit of the capacity of the thermal capacitor 12 (FIG. 1) is reached at curve 68, where the desired cooling is only reached just as the air exits the thermal capacitor 12. Even if the thermal capacitor 12 has fully used up its heat-absorbing capacity during inhalation, the subsequent exhalation cools the porous material 16. The exhaled air enters at an exhalation temperature 70 that is about body temperature (37° C.) that is cooler than the elevated temperature of the porous material 16. The porous material is cooled for the next inhalation cycle when the heat contained in the porous material from the previous inhalation step is transferred back to the exhaled cool air which is expelled out of the apparatus.

The apparatus 10 advantageously provides cooling of very hot air to a temperature that is safe to breathe without relying on external power sources or outside cooling sources such as ice baths or cooling fluids. The apparatus is of a size and weight such that it can be manually carried as part of a regular equipment issued to a user, even when the user is engaging in strenuous physical activity.

Figure 6:
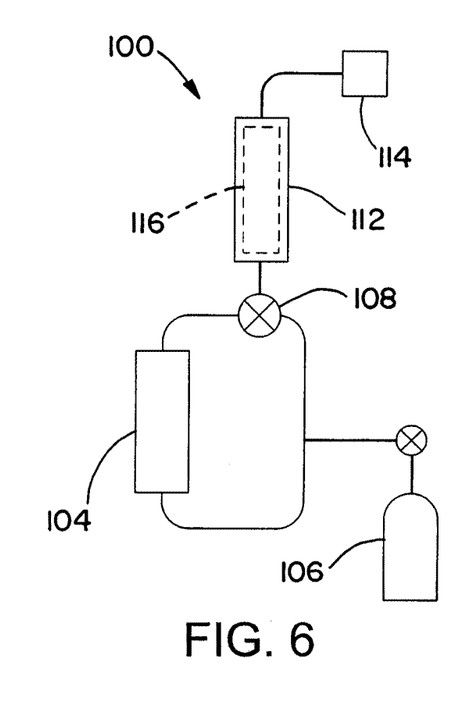
FIG. 6 is a schematic diagram of a breathing apparatus according to an alternate embodiment of the invention.

FIG. 6 shows a schematic embodiment of another embodiment, a breathing apparatus 100 that is a rebreather that circulates exhaled air through a scrubber 104 that removes carbon dioxide from the exhaled air, before the air is inhaled again by the user. An oxygen tank 106 or other oxygen source is used to provide additional metered oxygen for the air to be inhaled.

The apparatus 100 may include a valve 108 that directs exhaled air to the scrubber 104, and draws air for inhalation from both the oxygen tank or bottle 106 and the scrubbed air that has passed through the scrubber 104. One problem is that the scrubber 104 generates a significant amount of heat when carbon dioxide reacts with the alkali scrubber material (typically soda-lime or lithium hydroxide). To cool the heated scrubbed air, a thermal capacitor 112 may be placed between the valve 108, and a respiratory conduit 114 that the user breathes into and out of. The thermal capacitor 112 may be similar to the thermal capacitor 12 (FIG. 1), and the respiratory conduit 114 may be similar to the respiratory conduit 14 (FIG. 1), such that common details regarding the thermal capacitor 12 and the respiratory conduit 14 will not be repeated here. The thermal capacitor 112 may have a different size or shape than the thermal capacitor 12, for example because there is not a need for the thermal capacitor 112 to have as much cooling capacity as the thermal capacitor 12.

The thermal capacitor 112 cools incoming air (air being inhaled by the user) that has been heated by passing through the scrubber 104. Exhaled air passes through the thermal capacitor 112, cooling a porous material 116 of the thermal capacitor 112. Thus the thermal capacitor 112 functions in a manner similar to that of the thermal capacitor 12 (FIG. 1), cooling incoming air to a safe temperature for inhalation, without relying on external cooling (such as ice packs or other thermal sinks) or external power of any sort.

The thermal capacitor 112 can be incorporated into the breathing apparatus 100 in any of a variety of locations in the rebreather apparatus 100. For example, the thermal capacitor 112 may be a disk that is placed between the conduit 114 and the oxygen tank or bottle 106, somewhere in a hose or other suitable location. The thermal capacitor 112 may be a series of layers of mesh material, a specific example being an oval disk, 4.8 cm by 2.2 cm (1.88 inches by 0.88 inches), having 17 stacked layers of mesh material, with a total thickness of 0.76 cm (0.3 inches). Alternatively the thermal capacitor 112 may be wrapped around the oxygen bottle 106 or another structure of the apparatus 100.

Figure 7:
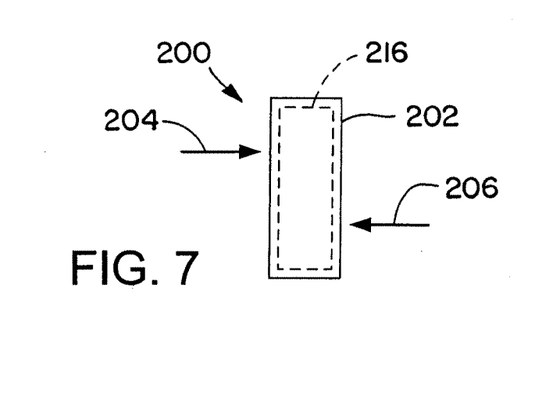
FIG. 7 is a schematic diagram of a system for reducing temperature fluctuations in a periodic gas flow, according to another alternate embodiment of the invention.

FIG. 7 illustrates the broader concept of a system 200 that includes a thermal capacitor 202 used to reduce temperature fluctuations in a periodic gas flow. The periodic gas flow provides gas flow alternately in a first direction 204 and a second direction 206. The periodic gas flow may be any of a wide variety of gas flows. The respiratory gas flows described above are examples. Another example is a ventilation system of a building, which may alternate exhausting inside air, and bringing in fresh air from outside the building.

The periodic gas flow is directed through the thermal capacitor 202, with porous material 216 in the thermal capacitor 202 being used to reduce temperature fluctuations in the gas flow. The thermal capacitor 202 cools the flow in the first direction 204, and warms the flow in the second direction 206. The porous material 216 may have a time constant, a lumped thermal capacitance of the porous material divided by a thermal resistance of the porous material, that is at least a period of the periodic gas flow. The thermal time constant is discussed above with regard to the porous material 16 (FIG. 1).

The system 200 may reduce thermal loads on a system, such as a HVAC system, by using outgoing building air to heat or cool incoming air. The system 200 may also be used for controlling temperature in other periodic gas flows. The amount of porous material 216 and the size of the thermal capacitor 202 may be much greater than for the other (portable) embodiments described herein.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A wearable breathing apparatus for controlling temperature of air inhaled by a user, the breathing apparatus comprising:
   a respiratory conduit that is adapted for the user of the apparatus to inhale and exhale through; and
   a thermal capacitor operatively connected to the respiratory conduit; wherein the thermal capacitor and the respiratory conduit are adapted such that inhaled air and exhaled air passing through the respiratory conduit also passes through a porous material of the thermal capacitor;
   wherein the porous material has a time constant, a lumped thermal capacitance of the porous material (mass of the porous material multiplied by specific heat of the porous material) multiplied by a thermal resistance of the porous material (the reciprocal of the heat transfer coefficient multiplied by the surface area available for heat transfer), that is at least 0.5 seconds;
   wherein the respirator conduit includes one or both of a mask configured to be placed over a mouth and a nose of the user, and a mouthpiece adapted to be placed in the mouth of the user;
   wherein the thermal capacitor includes a casing, external of the one or both of the mask and the mouthpiece, that surrounds the porous material;
   wherein the porous material includes one or more of a woven material, a mesh material, a bed of spheres, particles, and/or pellets, and/or a monolith; and
   wherein the porous material has a void fraction of at least 0.3.

2. The apparatus of claim 1, wherein the respirator conduit includes the mask.

3. The apparatus of claim 1, wherein the respirator conduit includes the mouthpiece adapted to be placed in the mouth of the user.

4. The apparatus of claim 1, wherein the thermal capacitor has a length in a flow direction along which air passes through the thermal capacitor, that is 12.7 cm (5 inches) or less.

5. The apparatus of claim 1, wherein the porous material includes the woven material and/or the mesh material.

6. The apparatus of claim 5, wherein the woven and/or mesh material includes a polymer material.

7. The apparatus of claim 1, wherein the breathing apparatus is unpowered and does not include a cooling fluid.

8. The apparatus of claim 1, wherein the thermal capacitor has a mass of 0.45 kg or less.

9. The apparatus of claim 1, wherein the apparatus is part of a rebreather that includes a scrubber in fluid communication with the thermal capacitor, with the scrubber removing at least some of the carbon dioxide from the exhaled air, and the thermal capacitor cooling the inhaled air, at least some of which has passed through the scrubber.

10. A method of cooling breathing air inhaled by a person, the method comprising:
    passing the air to be inhaled through a porous material of a thermal capacitor, with the porous material cooling the air to be inhaled; and
    exhaling air through the porous material, thereby cooling the porous material;
    wherein the porous material has a time constant, a lumped thermal capacitance of the porous material (mass of the porous material multiplied by specific heat of the porous material) multiplied by a thermal resistance of the porous material (the reciprocal of the heat transfer coefficient multiplied by the surface area available for heat transfer), that is at least 0.5 seconds;
    wherein the porous material includes one or more of a woven material, a mesh material, a bed of spheres, particles, and/or pellets, and/or a monolith; and
    wherein the porous material has a void fraction of at least 0.3.

11. The method of claim 10, wherein the cooling the air to be inhaled cools the air from 120° C. or higher, to 48° C. or lower.

12. The method of claim 11,
    wherein the thermal capacitor is part of a breathing apparatus that is capable of continuing to cool inhaled air from 120° C. or higher, to 48° C. or lower, for at least 15 minutes; and
    wherein the inhaling and the exhaling continue to alternate for at least 15 minutes.

13. The method of claim 11,
    wherein the porous material is a woven and/or mesh material; and
    wherein the passing the cooling the air includes passing the air through the mesh material to cool the inhaled air to 48° C. or lower.

14. The method of claim 11,
    wherein the porous material is a bed of particles; and
    wherein the passing the cooling the air includes passing the air through the particles to cool the inhaled air to 48° C. or lower.

* * * * *